United States Patent [19]

Dornhagen et al.

[11] Patent Number: 4,802,956

[45] Date of Patent: Feb. 7, 1989

[54] PROCESS FOR THE PURIFICATION OF DIMETHYLETHER BY DISTILLATION

[76] Inventors: Horst Dornhagen; Hartmut Hammer; Ewald Meisenburg, all of Union Kraftstoff AG, Postfach 1663, D-5047 Wesseling, Fed. Rep. of Germany

[21] Appl. No.: 933,035

[22] Filed: Nov. 20, 1986

[51] Int. Cl.$^4$ .................. B01D 3/14; C07C 41/42
[52] U.S. Cl. ..................... 203/42; 203/71; 203/75; 203/80; 203/82; 203/DIG. 19; 568/698; 568/699
[58] Field of Search ............. 203/DIG. 19, DIG. 9, 203/42, 99, 98, 75, 78, 71, 82, 84, 80; 568/699, 698

[56] References Cited

U.S. PATENT DOCUMENTS

| 2,443,906 | 6/1948 | Guinot et al. | 568/698 |
| 2,497,601 | 2/1950 | Guinot | 568/699 |
| 3,356,590 | 12/1967 | Johnson | 203/DIG. 9 |
| 3,847,756 | 11/1974 | Statman et al. | 203/96 |
| 4,260,813 | 4/1981 | Kametaka et al. | 203/DIG. 19 |
| 4,560,807 | 12/1985 | Murai et al. | 203/DIG. 19 |

FOREIGN PATENT DOCUMENTS 0124078 4/1983 European Pat. Off. .

Primary Examiner—Wilbur Bascomb
Attorney, Agent, or Firm—Connolly and Hutz

[57] ABSTRACT

The instant invention relates to a process for the purification of dimethylether, which contains impurities, by feeding a mixture which contains the dimethylether at specific trays to a distillation column and withdrawal of the dimethylether and of impurities at specific trays of the same column.

7 Claims, 2 Drawing Sheets

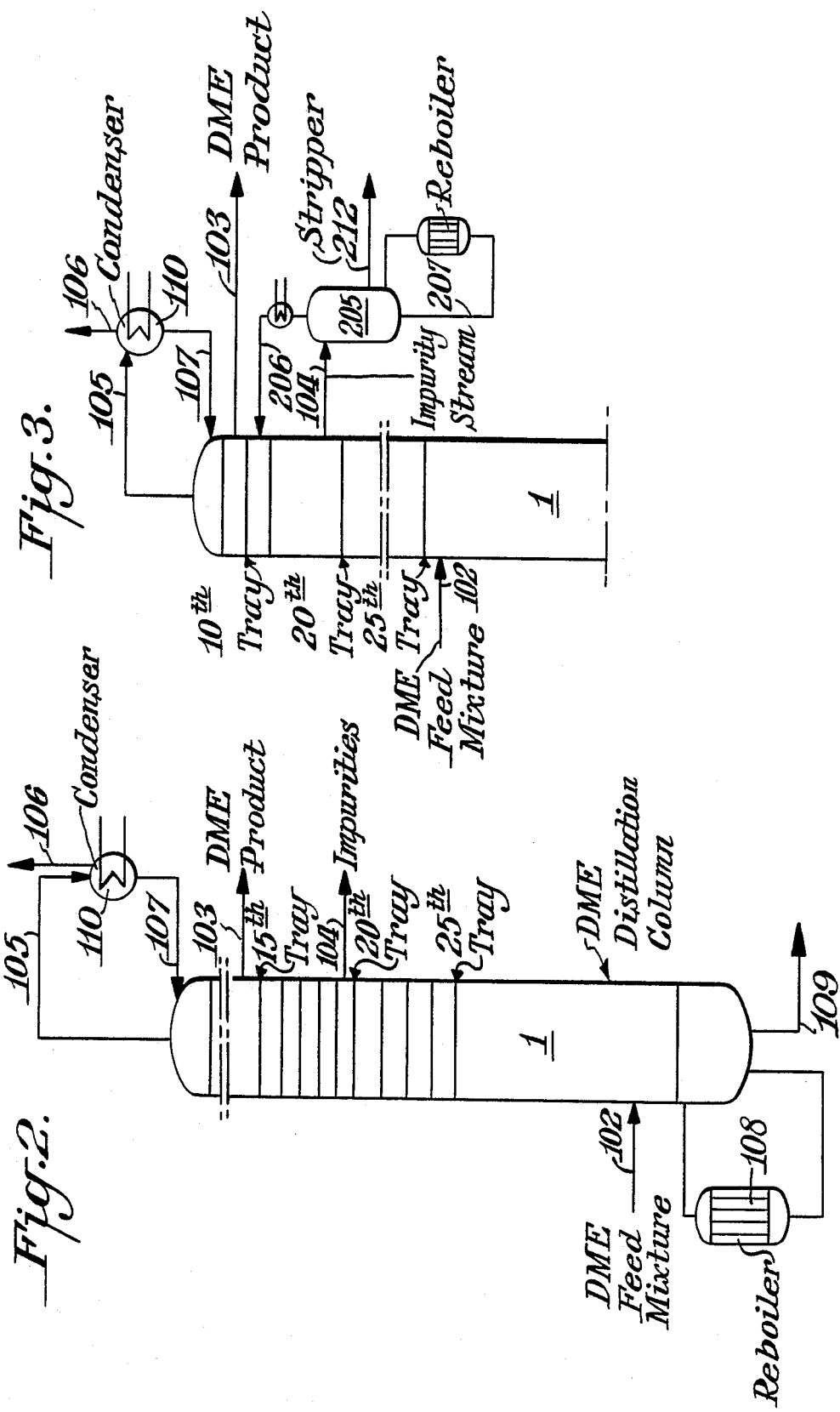

PROCESS FOR THE PURIFICATION OF DIMETHYLETHER BY DISTILLATION

BACKGROUND OF THE INVENTION

1. Field of the Invention

The instant invention relates to a process for the purification of dimethylether, which contains impurities, by feeding a mixture which contains the dimethylether at specific trays to a distillation column and withdrawal of the dimethylether and of impurities at specific trays of the same column.

2. Description of the Prior Art

Before the development of low pressure processes for the production of methanol, dimethylether was obtained as a side-product of high pressure methanol processes, usually in a quantity of 2 to 3 weight-% based on the total quantity of products withdrawn from the methanol synthesis reactor. Dimethylether was separated from raw methanol together with other impurities as first runnings in the distillation unit for the production of pure methanol.

After introduction of low pressure methanol processes, which form only negligible quantities of dimethylether, specific processes for the synthesis of dimethylether by catalytic dehydration of methanol were developed.

Numerous catalysts and processes are disclosed in the patent literature.

According to DE-PS No. 680 328 aliphatic ethers are obtained by heating alcohols in the presence of $ZnCl_2$. Other suitable catalysts for the production of ethers from alcohols are according to British Patent Publications No. 332 756, No. 350 010 and No. 403 402, U.S. Pat. No. 1,873,537 and French Patent Publication No. 701 335 ferric chloride, copper sulfate, stannic chloride, manganese chloride, aluminum chloride and sulfate, chromium sulfate, alums, thorium derivates, aluminum oxide, titanium oxide, barium oxide, silica gel or aluminum phosphate.

The synthesis of dimethylether directly from synthesis gas ($CO+H_2$) has also been described (DE-PS No. 23 62 944, DE-PS No. 27 57 788 and DE-PS No. 32 20 547).

The technically most important catalysts have proven to be according to DE-PS No. 28 18 831, DE-OS No. 32 01 155, European Patent Application No. 0 099 676 and European Patent Application No. 0 124 078 in particular aluminum oxide and aluminum silicate catalysts with and without doping.

The raw dimethylether thus obtained contains reaction water, unconverted methanol as well as small quantities of impurities like for example methylformate, hydrocarbons, amines and sulfides.

In these production plants raw dimethylether is worked up in two consecutive distillation columns, in the first of which, dimethylether is distilled off under pressure and in the second of which unconverted methanol is separated and recycled.

Thus in European Patent Application No. 0 124 078 a process is disclosed, according to which in a first pressurized column, dimethylether is separated as a sidestream, whereas in a second column, which is operated at a lower pressure, the impurities with boiling points between methanol and dimethylether are withdrawn as a head product. Unconverted methanol is separated also in the second column as a side-product.

Although this process leads to dimethylether of high purity, it has the considerable economic disadvantage, that not only the first but also the second column have to be provided with a high number of trays, resulting in high capital expenditure and in particular in high operating costs. Furthermore there is a risk that impurities with boiling points between dimethylether and methanol remain at least in small quantities in the first column resulting in contamination of dimethylether.

Since dimethylether is of increasing importance as a propellant in aerosol sprays, very high demands are made on the purity of dimethylether for certain applications. In particular for cosmetic, human and household applications dimethylether must be free of irritating substances. Furthermore dimethylether must be odorless for these applications. Thus the problem existed, to make available on the one hand a more economical production process for dimethylether compared to the state of the art and on the other hand to produce dimethylether in high purity and practically quantitatively based on feed methanol.

SUMMARY OF THE INVENTION

The problem outlined above has been solved by applicant in an non-obvious, surprising manner by the inventive process for the production of dimethylether of high purity by distillation of dimethylether which contains impurities and/or distillation of mixtures which contain dimethylether, methanol and impurities, characterized in that the dimethylether-mixture which contains the impurities is fed to a distillation column below the twentyfifth tray (from the top of the column) at one or several trays, that pure dimethylether is withdrawn above the fifteenth tray, preferably above the tenth tray (from the top of the column) and that the impurities are withdrawn at a tray, which is at least five trays above the (highest) tray which is used as feed tray for the feed mixture containing dimethylether and impurities.

DESCRIPTION OF THE PREFERRED EMBODIMENTS

Figure 1:
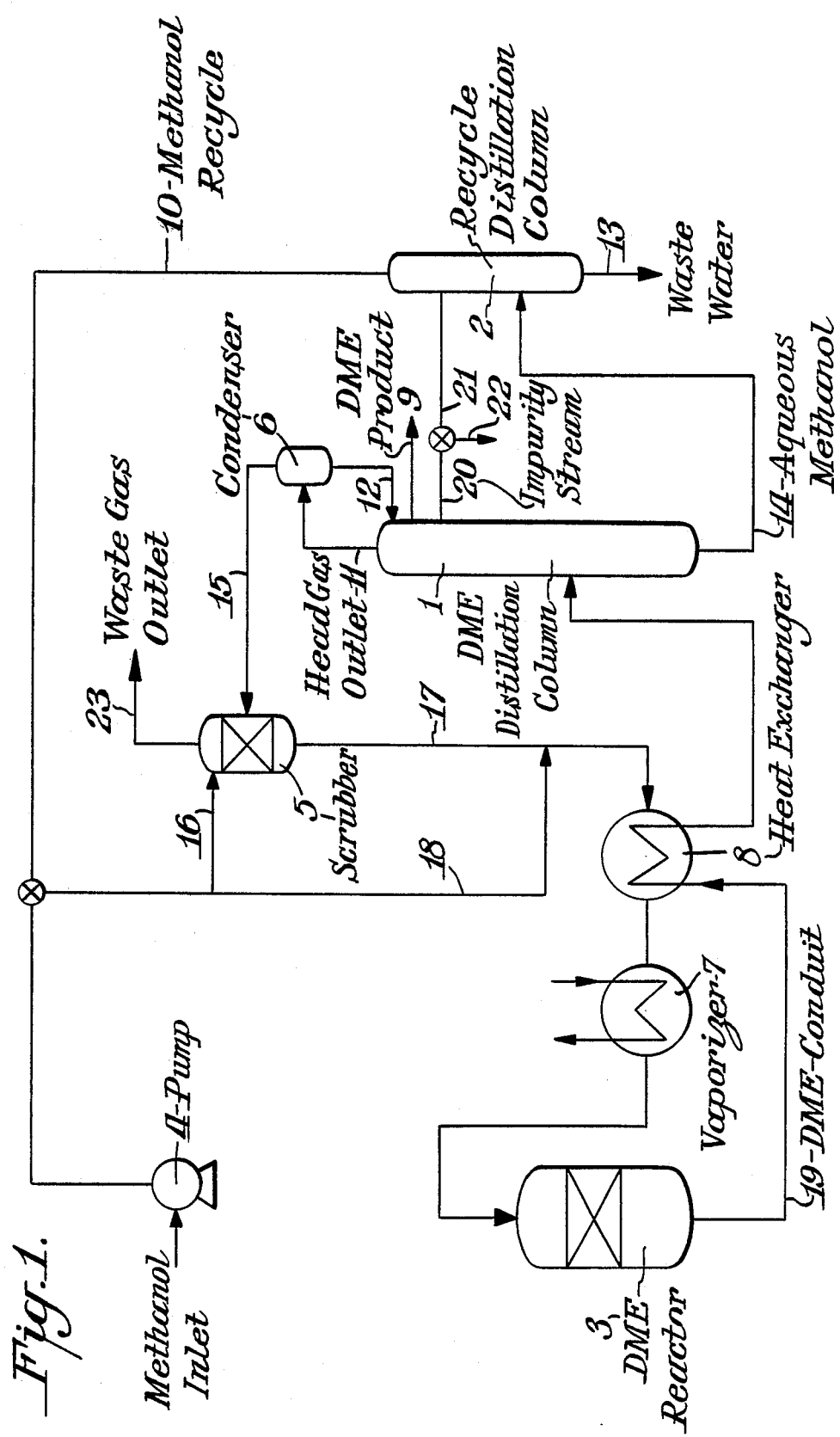

Raw methanol from a high pressure methanol production unit as well as dimethylether which is catalytically produced from methanol, contain, as outlined already above, numerous impurities, some of which have strong odors.

In high pressure methanol production units raw methanol is obtained, which usually contains 2 to 3, however may contain up to 5 weight-% of dimethylether. In dimethylether synthesis from raw or pure methanol, usually mixtures which contain 20 to 80 weight-% of dimethylether based on methanol feed are obtained at the synthesis reactor exit, depending on operating conditions. In addition the raw dimethylether contains impurities mentioned above, reaction water and unconverted methanol.

The boiling points of the impurities for example of dimethylamine (6.9° C.), dimethylsulfide (37.3° C.), methylmercaptane (5.8° C.), formic acid (100.75° C.), formic acid methylester (31.5° C.), formaldehyde (−21° C.), formaldehyde dimethylacetale (45.5° C.) or acetic acid methylester (56.95° C.) as well as their solubilities and vapor pressures in the product mixture, are very different from each other. Since the subjectively noticed intensities of odors of the individual impurities are also very different, the solution of the problem of producing very pure dimethylether in nearly quantitative yield by a process which is more economical with regard to the state of the art, is very difficult.

Applicant therefore has found as a result of numerous tests during several years in laboratory, pilot plant and technical unit, that the problem identified above can be solved by the inventive purification process in a particularly economical way. It is obvious for the artisan that according to the instant invention the second column has only to be a distillation column with a small number of trays, since only methanol with a boiling point of 64.7° C. has to be separated from water.

According to the instant invention, distillation columns of the state of the art can be used, the size of which depending on the capacity of the unit. The trays used can be trays in accordance with the state of the art, like for example valve trays, sieve trays, bubble trays and others. In principle also filling and packing material can be used as rectification devies like for example ceramics, glass materials, wire packing and others, whereby the inventive location of the feed introduction and the locations for withdrawal of dimethylether and impurities can be calculated in accordance with the tray-locations disclosed in the instant invention.

In FIG. 1 as an example a unit for production and purification of dimethylether is represented.

In FIG. 2 as an example a distillation column for the production of pure dimethylether is represented.

In FIG. 3 as an example this column is equipped with a side-stripper.

The investigations of applicant have led to the result that in order to solve the problem outlined above, namely the production of highly pure dimethylether in nearly quantitative yield based on methanol feed, in a particularly economical way, introduction of the feed into the column has to take place below the twentyfifth (25th) tray (from the top of the column) at one or several trays. In case the feed is introduced at a tray closer to the top of the column, the purity of dimethylether desired, is not obtained, in particular with regard to absence of odor.

Furthermore pure dimethylether has to be withdrawn according to the invention above the fifteenth (15th) tray, preferably above the tenth (10th) tray (from the top of the column). This can be for example the sixth (6th) tray, but also the first (1st) to fifth (5th) or sixth (6th) to fifteenth (15th) tray. Alternatively condensate at the head of the column can be withdrawn. Also several trays can be used.

The investigations of applicant have shown furthermore that components with boiling points between those of methanol and dimethylether can be withdrawn from the same column at one or several trays located at least 5 trays above the (highest) feed tray, where feed containing contaminated dimethylether and/or a mixtures containing dimethylether, methanol and impurities is introduced into the column.

If a feed is introduced, which for example contains 1-5 weight-% of dimethylether, methanol and other components with boiling points between those of methanol and dimethylether and optionally water and other oxygen containing hydrocarbons like for example alcohols with a number of C-atoms >1, the column is operated with a reflux ratio of 1:1 to 1:25, depending on the portion of dimethylether. Thus in case of for example a dimethylether portion of 1 weight-%, the reflux ratio can be 1:20.

A reflux ratio of for example 1:1 means that the quantity of dimethylether withdrawn is equal to 1 part, whereas the quantity of vapor for condensation at the head of the column is 1+1 parts.

In case of a dimethylether content of for example 3-4 weight-% a reflux ratio of 1:5-8 is preferred. These quantities of dimethylether correspond to the quantities present in raw methanol of high pressure methanol production units. Dimethylether can only be obtained in a very pure state in nearly quantitative yield if the inventive feed tray(s) and trays for withdrawal of dimethylether and impurities are used.

In case of for example a dimethylether content of 20 to 80 weight-% and in the presece of methanol and other components with boiling points between those of methanol and dimethylether and optionally of water and other oxygen containing hydrocarbons like for example alcohols with a number of C-atoms >1, the reflux ratio according to the instant invention is 1:0.4 to 1:5, preferably of 1:1 to 1:2.5 depending on the dimethylether content.

In case of for example a mixture, which contains 60 weight-% of dimethylether, 15 weight-% of methanol and additionally water and impurities, a reflux ratio of 1:1.5 to 1:2.5 can be used.

These feeds are typical mixtures obtained by the catalytic conversion of methanol to dimethylether with $Al_2O_3$-respectively $Al_2O_3/SiO_2$-catalysts at the exit of the syntheses reactor.

If the dimethylether portions are between 5 to 20 weight-% or higher than 80 weight-%, the inventive reflux ratios are to be chosen on the basis of the ratios disclosed.

The distillation column for the purification of dimethylether is operated in general at a pressure of 5-10 bar, whereby in case of a synthesis reactor preceeding the column, the pressure of the column is preferably adapted to the pressure of the synthesis reactor. Pressures outside of this range can also be used according to the invention.

Throughput is, as usual, determind by capacity of the column, heat applied and reflux ratio.

In order to obtain pure dimethylether in nearly quantitative yield, in particular in case of low portions of dimethylether in the feed, the gas mixture withdrawn at the head of the column, which contains in general $CO_2$, $N_2$, hydrocarbons and small quantities of dimethylether, can be washed according to the invention. Suitable washing liquids are for example methanol and/or bottoms of the dimethylether distillation column. The washing liquid which contains dimethylether can be recycled to the distillation column or to the dimethylether synthesis reactor. Washing can be carried out in direct current or countercurrently. The latter procedure is prefered.

Furthermore the impurities withdrawn from the column can additionally be stripped in a side-stripper, whereby dimethylether separated by stripping is recycled to the column. By this procedure, dimethylether withdrawn with the impurities can practically quantatively recycled to the column.

EXAMPLES AND FIGURES

The following examples have been carried out in continuous operation. EXAMPLE 1

4000 kg/h of a mixture consisting of 2400 kg of dimethylether, 580 kg of methanol, 910 kg of water and 110 kg of impurities are fed at the 49th tray (from the top of the column) to a distillation column containing 65 valve trays.

The column is operated at 8.5 bar. The reflux ratio is 1:1.9.

At the head of the column 30 m³ of a gas mixture are withdrawn, which essentially contain $CO_2$, $N_2$, hydrocarbons and a small quantity of dimethylether.

At the sixth (6th) tray of the column (from the top of the column) 2385 kg/h of pure dimethylether are withdrawn with a methanol content of <10 ppm. At the 44th tray (from the top of the column) 90 kg/h of impurities are withdrawn. 10 kg/h of higher boiling impurities (than methanol), 580 kg/h of methanol and 910 kg/h of water are withdrawn from the bottom of the column and fed to a second column, where methanol is separated from water by distillation.

EXAMPLE 2

Example 1 is repeated, however the impurities withdrawn are fed to a side-stripper.

2395 kg/h of pure dimethylether and 80 kg/h of impurities at the exit of the side-stripper are obtained.

Example 3

61000 kg/h of a mixture consisting of 55000 kg methanol, 2000 kg of dimethylether, 3500 kg of water and 500 kg of impurities are fed to a distillation column containing 100 valve trays.

The reflux ratio is 1:7.

The mixture is fed to the column at the 35th tray (from the top of the column).

At the ninth (9th) tray (from the top of the column) 1996 kg/h of dimethylether are withdrawn.

At the 30th tray (from the top of the column) 302 kg/h of impurities are withdrawn at the exit of the stripper.

55000 kg/h of methanol, 3500 kg/h of water and 200 kg/h of impurities, which consist essentially of higher alcohols, are withdrawn fromt the bottom of the column. The pressure in the column is between 6 and 8 bar.

Overhead gas is washed countercurrently with methanol. The washing methanol containing small quantities of dimethylether is fed to the column.

Example 4

4000 kg/h of a mixture consisting of 800 kg of dimethylether, 2825 kg of methanol, 300 kg of water and 75 kg of impurities, boiling between methanol and dimethylether, are fed at the 48th tray (from the top of the column) to a column containing 70 bubble trays. The reflux ratio is 1:5.5.

At the fourth (4th) tray (from the top of the column) 796 kg/h of dimethylether are withdrawn.

At the fortieth (40th) tray (from the top of the column) 77 kg/h of impurities are withdrawn. From the bottom of the column 2825 kg/h of methanol and 300 kg/h of water are withdrawn.

EXAMPLE 5

2000 kg/h of a mixture containing 1750 kg of dimethylether, 100 kg of methanol, 100 kg of water and 50 kg of impurities are fed to the 38th tray of a distillation column (from the top of the column) which contains 45 bubble trays. The reflux ratio is 1:1.

1745 kg/h of dimethylether are withdrawn at the third (3rd) tray of the column (from the top of the column) and 48 kg/h of impurities are withdrawn at the thirtythird (33rd) tray of the column (from the top of the column). 100 kg/h of water, 100 kg/h of methanol and 5 kg/h of impurities which have higher boiling points than methanol, are withdrawn from the bottom of the column.

In FIG. 1 the distillation column for the purification of dimethylether is represented by (1). Very pure dimethylether is withdrawn at (9). Head gas passes through (11) to condenser (6). Reflux passes through (12) to column (1). Waste gas passes through (15) to scrubbing unit (5), where the gas is washed with methanol (16). In principle also other washing liquids can be used, like for example raw methanol or bottoms of column (1), whereby in the latter case the washing liquid containing dimethylether is recycled to column (1). Small quantities of dimethylether combined with methanol pass through (17) to the syntheses reactor for dimethylether (3). Waste gas leaves the unit through (23). The main quantity of methanol feed is pumped by pump (4) through (18), heat exchanger (8) and vaporizer (7) to (3). Synthesis product (19) passes through (8) to (1).

At (20) impurities with boiling points between those of methanol and dimethylether are withdrawn and pass through (22) for example to an incineration. Bottoms of (1), which essentially contain water and methanol pass to methanol distillation column (2). (2) is operated in general at atmospheric pressure. In principle, pressures can also be applied which are somewhat higher or lower than the pressure in (1). In general however the pressure in (2) is below that of (1). Methanol is withdrawn through (10) and recycled to the synthesis reactor. Waste water is withdrawn through (13). If required, impurities with boiling points higher than methanol can be withdrawn through (21).

In FIG. 2 (1) represents the distillation column for the production of pure dimethylether. Feed is introduced through (102). Pure dimethylether is withdrawn through (103). Impurities are withdrawn through (104). Head product passes through (105) to condenser (110). Reflux passes through (107) to column (1). Waste gas leaves the unit at (106) and (108) represents the reboiler cycle. At (109) bottoms are withdrawn.

In FIG. 3 the impurities pass through (104) to stripper (205), which is equipped with reboiler cycle (207). Dimethylether which is separated by stripping, passes through (206) to column (1). Feed is added at (102). Pure dimethylether is withdrawn at (103). Head gas passes through (105) to condenser (110). Reflux passes through (107) to column (1). At (212) the impurities which are stripped of dimethylether are withdrawn.

According to the instant inventions highly pure dimethylether is produced in almost quantitative yield based on methanol feed. Dimethylether thus obtained is free of odor, contains less than 10 ppm of methanol, and a maximum of 0.1 weight-% of hydrocarbons. Its purity is at least 99.9 weight-% of dimethylether. Dimethylether obtained by the instant invention is excellently suited for any application in any aerosol spray as a propellant.

Compared to the state of the art only one column with high rectification efficiency is needed according to the instant invention. The second column serves in contrast to the state of the art only for the separation of methanol from water. Thus a relatively low rectification efficiency is needed.

In addition the inventive process permits the separation of impurities with boiling points higher than methanol in the second column. As a result waste water from the bottom of the second column contains only small amounts of impurities and can relatively easily be purified by waste water treatment.

What we claim is:

1. A process for the purification of dimethylether by distillation of a dimethylether feed mixture which contains methanol and impurities which comprises feeding the feed mixture which contains dimethylether, methanol and impurities into a distillation column containing a plurality of trays below the twentyfifth tray from the top of the column, withdrawing pure dimethylether from the column above the fifteenth tray from the top of the column, withdrawing an impurity fraction stream which contains impurities with lower boiling points than that of methanol from the column at least five trays above the tray at which said mixture is fed into the column, and withdrawing head gases from the top of the column and methanol from the bottom.

2. A process according to claim 1 wherein pure dimethylether is withdrawn from the column above the tenth tray from the top of the column.

3. A process according to claim 1, wherein the feed mixture comprises 1–5 weight-% of dimethylether, methanol and impurities with boiling points between those of methanol and dimethylether and the distillation column is operated at a weight ratio of withdrawn dimethyl-ether to vapor for condensation at the column head of 1:1+1 to 1:25+1.

4. A process according to claim 1, wherein the feed mixture comprises 20–80 weight-% of dimethylether, methanol, and impurities with boiling points between those of methanol and dimethylether and the distillation column is operated at a weight ratio of withdrawn dimethylether to vapor for condensation at the column head of 1:0.4+1 to 1:5+1.

5. A process according to claim 4 wherein the ratio is 1:1+1 to 1:2.5+1.

6. A process according to claim 1 or 3 or 4 wherein the head gases withdrawn from the top of the column are $CO_2$, $N_2$, light hydrocarbons and small quantities of dimethylether and the withdrawn head gases are scrubbed by co-current or counter-current with methanol.

7. A process according to claim 1 or 3 or 4 wherein the impurity fraction stream withdrawn is treated in a side-stripper to remove dimethylether which when separated is recycled to the distillation column.

* * * * *